United States Patent

Bergstrom et al.

Patent Number: 6,023,332
Date of Patent: Feb. 8, 2000

[54] DEVICE AND METHOD FOR MEASURING BIREFRINGENCE IN AN OPTICAL DATA CARRIER

[75] Inventors: Hakan Bergstrom, Lund; Ulf Wilhelmson, Malmo; Lars Jonsson, Lund, all of Sweden

[73] Assignee: Ifunga Test Equipment B.V., Netherlands

[21] Appl. No.: 09/180,261

[22] Filed: Jan. 14, 1999

[30] Foreign Application Priority Data

May 9, 1996 [SE] Sweden .................................. 9601760

[51] Int. Cl.[7] ..................................... G01J 4/00
[52] U.S. Cl. ......................... 356/365; 356/364; 356/367; 356/368; 356/369
[58] Field of Search .................... 356/365, 364, 356/367, 368, 369

[56] References Cited

U.S. PATENT DOCUMENTS

| | | | |
|---|---|---|---|
| 5,227,623 | 7/1993 | Heffner | 356/364 |
| 5,257,092 | 10/1993 | Noguchi et al. | 356/367 |
| 5,450,200 | 9/1995 | Imagawa et al. | 356/364 |
| 5,864,403 | 1/1999 | Ajji et al. | 356/365 |

*Primary Examiner*—Frank G. Font
*Assistant Examiner*—Roy M. Punnoose
*Attorney, Agent, or Firm*—Greer, Burns & Crain, Ltd.

[57] ABSTRACT

A device for measuring birefringence in an optical data carrier has a laser light source with a polarization modifier, a beamsplitter, a polarizer, a photodetector, and a controller operatively connected to the photodetector. The laser light source illuminates various spots on the optical data carrier by means of a laser beam. The photodetector receives a reflected laser beam, converts it into an electric signal and supplies this signal to the controller, which determines a value for the birefringence in the illuminated spot on the optical data carrier. Furthermore, the device is provided with a transparent reference element with known birefringence properties, a mirror, and for directing the laser beam towards the reference element in a first calibration position; directly towards the mirror in a second calibration position; and towards the optical data carrier during non-calibration time. In the first calibration position the controller calculates a first calibration value from the signal received from the photodetector, said first calibration value corresponding to a given birefringence in the optical data carrier, and in the second calibration position the controller calculates a second calibration value, corresponding to a situation essentially without any birefringence at all in the optical data carrier. These calibration values are used for determining the birefringence in a given spot on the optical data carrier.

9 Claims, 1 Drawing Sheet

DEVICE AND METHOD FOR MEASURING BIREFRINGENCE IN AN OPTICAL DATA CARRIER

TECHNICAL FIELD

The present invention relates to a device and a method for measuring birefringence in an optical data carrier. The device comprises a laser light source provided with polarization modifying means, a beamsplitter, a polarizer, a photodetector, and a controller operatively connected to the photodetector, said laser light source being arranged to illuminate various spots on the optical data carrier by means of a laser beam through the beamsplitter and the polarizer, said photodetector being arranged to receive a laser beam reflected from the optical data carrier, convert it to an electric signal and supply the signal to the controller, and said controller being arranged to determine from the electric signal a birefringence value for the illuminated spot on the optical data carrier.

DESCRIPTION OF THE PRIOR ART

A common type of optical data carriers as described above is compact discs (CD). These are available in various kinds, such as CD-Audio (containing for instance music), CD-ROM (permanent read-only memory for computers), CD-I (interactive CD), and Photo-CD (containing digital photographs). The term compact disc will be used throughout the entire document to represent any given kind of optical compact disc—including those kinds not explicitly mentioned here. As CD-applications are becoming increasingly common in our society, there is an increasing need for reliable equipment for measuring various manufacturing parameters, so as to ascertain a continuous and high quality for the compact discs produced.

An important parameter to be monitored by manufacturers of compact discs is the optical birefringence in the plastic layer of the compact disc. To be able to read data stored on a compact disc or any other optical medium, it is common in some applications to use circularly polarized laser light, which is emitted to the compact disc from a laser diode. Even if the light has a perfect circular polarization before it reaches the compact disc, the reflected light will have a more or less elliptical polarization, due to the fact that light components with different polarizations are retarded, with respect to the phase, to different extents in the plastic layer of the compact disc—the so-called birefringence phenomenon. The intensity of the detected signal will be lower, if the light has elliptical polarization than if the light would have had a perfect circular polarization. Furthermore, if the polarization of the light is too elliptical, i.e. if the birefringence in the plastic layer of the compact disc is too large, the reading of data will become uncertain.

Due to the problems above standards are provided for the maximum amount of birefringence acceptable for compact discs. Hence, in the Philips' standards a maximum birefringence for CD-Audio discs is set to a value corresponding to a phase retardation of 100 nm at a wave length of 780 nm. There are reasons to believe that this limit will be applicable also to future generations of compact discs.

As an example of previously known measuring methods a test arrangement according to the ANSI-standard for recordable optical media is schematically illustrated in FIG. 1. A diode laser 11 emits a laser beam to a measuring object represented by a compact disc 10. The laser light passes through a quarterwave plate 12 and a dielectric beam-splitter 13, before the light is given linear polarization in a polarizer/analyzer 14. The light reflected from the compact disc will again pass through the polarizer/analyzer 14. will then be reflected at the beamsplitter 13 and pass an interference filter 16, and finally be detected and converted to an electric signal by means of a photodetector 15. A controller not shown in the drawing analyzes the electric signal and determines a value for the birefringence in the relevant spot on the compact disc.

In the measuring system described above the laser light has linear polarization when arriving at the compact disc. This will lead to large errors when measuring small birefringence values. For instance, for zero birefringence—i.e. no birefringence at all in the measuring spot in question—a signal noise being incorrectly interpreted by the measuring system as a 1% modulation of the laser light when passing through the compact disc will result in a misleading birefringence value of 20 nm rather than 0 nm.

Previously known systems for measuring birefringence usually employ a laser, which emits circularly polarized light, since such circularly polarized light is desired at the measuring object, i.e. the compact disc in this case, for reasons set out below. However, these systems have a problem in that the polarization of the light emitted from the laser diode will, even if the light is emitted with a perfect circular polarization, be modified by the optical components between the source of light and the measuring object. Once the laser light reaches the measuring object, the polarization will no longer be circular but elliptical.

Elliptically polarized laser light will be retarded to different extents in different tensional directions of the compact disc, even if the birefringence in itself is constant in the measuring spot in question. As a result it is very difficult—or even impossible—to separate component-dependent influences on the measuring result from the actual phase retardation in the compact disc.

An additional shortcoming in previously known measuring systems is that no concern, or at least not enough concern, has been given to the systematic variations in the measuring result due to temperature-dependent properties of the components comprised in the measuring system. Even if a certain measuring system has been carefully calibrated at the time of manufacture, by means of for instance a Soleil-Babinet-compensator (which is a standard means for measuring the phase retardation of polarized light at a given wavelength), this does not guarantee the correctness of the measuring system during use in real life situations, since the temperature-dependent systematic variations may be large.

SUMMARY OF THE INVENTION

It is an object of the present invention to remedy the disadvantages and the shortcomings of previously known measuring systems as described above. In particular, it is an object of the present invention to provide internal calibration for a birefringence measuring system, so as to ensure a high degree of measuring accuracy for high as well as low birefringence values, despite environmental variations, such as temperature.

These objects are achieved by a device and a method with features according to the characterizing port of the appended independent patent claims.

BRIEF DESCRIPTION OF THE DRAWINGS

The invention will now be described in more detail, reference being made to the accompanying drawings, in which.

DETAILED DESCRIPTION OF THE INVENTION

Figure 2:
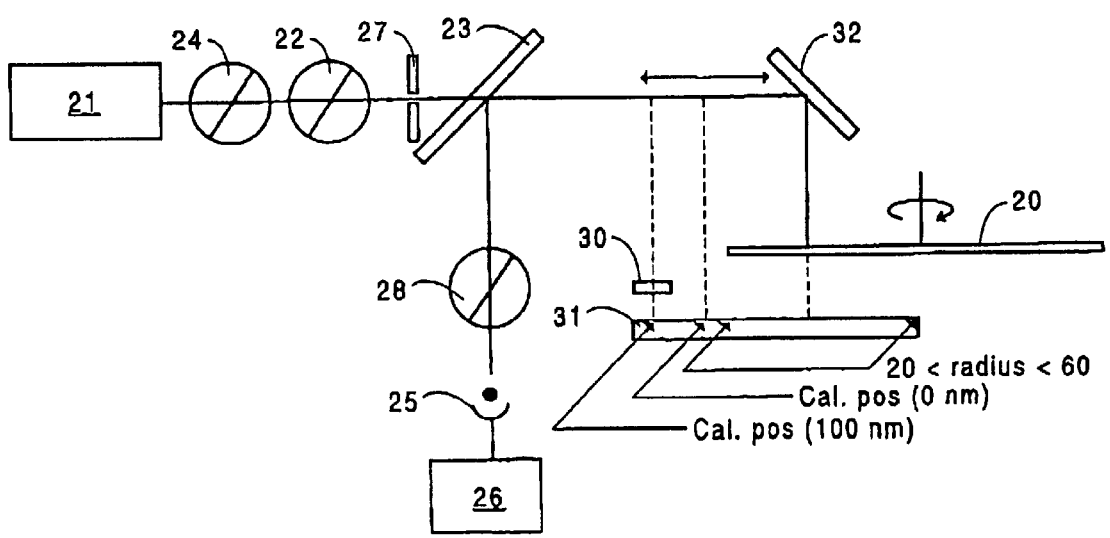
FIG. 2 is a schematic block diagram illustrating a measuring system according to a preferred embodiment of the invention.

FIG. 2 discloses a birefringence measuring system for an optical data carrier according to a preferred embodiment of the present invention. A conventional diode laser 21 is arranged to emit a circularly or slightly elliptically polarized laser light beam to an optical data carrier 20. In the following, the data carrier is described as a rotatable compact disc 20; it is to be understood, however, that the invention may be applied also to other kinds of optical data carriers. The laser light emitted from the laser 21 passes through a linear polarizer 24 and a quarterwave plate 22. A beam profile with homogeneous intensity is provided by means of an aperture 27 determining the size of the measuring spot. A measuring spot diameter of about 1 mm has proven suitable, but other values are equally possible depending on the desired resolution and operating speed of the system. The light then passes through a dielectric beamsplitter 23, which is arranged at an angle of 45 degrees and one side of which has an antireflection coating for providing a low degree of reflectivity (in this case: <0.4%), and then the light is reflected towards a dielectric mirror 32, which is arranged at an angle of 45 degrees. The mirror 32 is operatively connected to driving and control means not disclosed in the drawing for displacing the mirror along the radial direction of the disc 20. By maintaining the disc 20 in rotation by conventional means any given traces or spots on the disc may hence be illuminated by the laser light.

The linear polarizer 24 and the quarterwave plate 22 are arranged at certain positions in relation to each other and are provided with such optical properties, that the laser light will have a perfectly circular polarization when reaching the disc 20. Consequently, the tensional and directional dependent phase retardations described above are eliminated, which would occur for elliptically polarized incident light.

Figure 1:
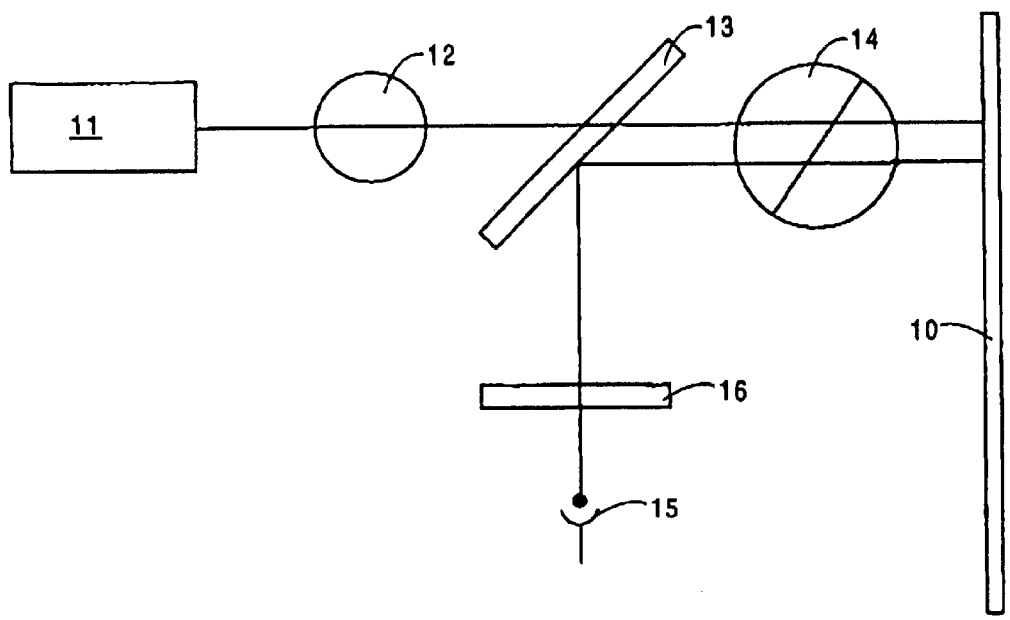
FIG. 1 is a schematic block diagram illustrating a prior, art measuring system

By means of the mirror 32 the circularly polarized incident light is directed towards the disc 20 during normal measurements. For internal calibration of the measuring system the mirror 32 also has a purpose of directing the laser light towards other means than the disc 20, namely a calibration plate 30 and a gold-plated mirror 31, respectively. The light reflected from either the disc 20, the calibration plate 30 and/or the golden mirror 31 will again be reflected at the mirror 32 and then be reflected by the beamsplitter 23—the second side of which is arranged to reflect a portion (in this case: 50%) of the incident light—towards a rotating polarizer 28. This rotating polarizer analyzes the polarization of the light, before it is detected by a photodetector 25. The photodetector converts the received light to a corresponding electric signal, which is supplied to a controller 26 operatively connected to the photodetector. The photodetector 25 may be provided with conventional band-pass filters, corresponding to the filter 16 in FIG. 1.

The controller 26, the operation of which will be described in more detail below, is preferably comprised by a microprocessor together with suitable pieces of hardware and software. According to the preferred embodiment of the invention a processor in the Intel 80486-family is used, but the functions of the controller may be realized in various ways, such as by means of dedicated and strictly hardware-based circuitry, by means of digital signal processors (DSP), or by using a conventional personal computer or workstation known per se from various industrial applications, as is readily realized by a man skilled in the art.

The analysis of the reflected light in the rotating polarizer 28 provides a maximum value as well as a minimum value for the intensity of the received light. By means of the calibration values described below the controller will compensate for equipment- or environment-dependent influences upon the measuring result, thereby providing a corrected or adjusted maximum value ($I_{max}$) as well as a minimum value ($I_{min}$) From these values the controller 26 is arranged to calculate a birefringence value BR for the current measuring spot on the disc 20:

$$BR = \lambda \cdot \left( \frac{1}{4} - \frac{1}{\pi} \arctan\left[ \sqrt{\frac{I_{min}}{I_{max}}} \right] \right) \quad [nm],$$

where $\lambda$ represents the wavelength of the laser light (in nm).

Thanks to the internal calibration of the measuring system described in the following, the controller may compensate for temperature-dependent phase retardations as well as polarization-dependent reflectivity of the optical components (beamsplitters, mirrors and polarizers) when calculating and determining a value for the real birefringence in the compact disc 20. The internal calibration is effectuated as described in the following.

The mirror 32 is displaced to a first calibration position, in which the incident laser light is reflected towards the calibration plate 30 described above. The calibration plate 30 has a known phase retardation, the exact values of which have been calibrated at the time of manufacture by means of for instance a Soleil-Babinet-compensator. Preferably, the material and the dimensions of the calibration plate are chosen in such a way, that the phase retardation of laser light at the wavelength in question (in this case: 780 nm) corresponds to 50% of the maximum permitted phase retardation (in this case: 100/2 nm=50 nm). Since the laser light will be reflected by the golden plate 31 below and hence will pass twice through the calibration plate, this value corresponds to the maximum permitted phase retardation or birefringence value (in this case: 2·50 nm=100 nm) The reflected light is detected by the photodetector 25, and the controller 26 may register the values for maximum and minimum light intensity corresponding to the known birefringence of the calibration plate 30.

According to the preferred embodiment of the present invention the calibration plate 30 is comprised by two crystalline quartz plates, the retardation of which almost neutralize each other. The diameter of the circular calibration plate is 8.0 mm, and the total thickness is 2.1 mm, but other dimensions are equally possible. When the laser light passes through the calibration plate, a rotation of phase occurs between the ordinary and the extraordinary polarization components of the light. According to the above this rotation of phase corresponds to a phase retardation of 50 nm at a laser light wavelength of 780 nm. Since the thickness of the material is dependent upon the temperature, the optical wavelength of the material will increase as a function of the temperature, but only the difference between the two polarizations is relevant. The exact value of the phase retardation or birefringence in the calibration plate does not have to be exactly 100 nm. The value will be calibrated by the manufacturer once and for all, and the controller 26 has access to this exactly calibrated value.

Once the first calibration value, corresponding to the maximum permitted birefringence, has been obtained according to the above, the mirror 32 is displaced to a second calibration position, wherein the incident laser light is immediately directed towards the gold-plated mirror 31. The golden mirror 31 will reflect the laser light with no phase retardation at all, whereby the controller 26 will register the values of maximum and minimum light intensity at zero refraction (no birefringence at all).

These two calibration values (a measuring value for maximum birefringence and a measuring value for no birefringence) are used by the controller 26 when measuring the birefringence of a given measuring object 20, wherein equipment- or temperature-dependent phase retardations will be eliminated by calibration. Hence, a traceable calibration with high accuracy is achieved thanks to the invention.

In addition to the components described above the measuring device may be provided with other components, which may be used for measuring parameters other than birefringence, such as skewness and reflectivity. It should be apparent to a man skilled in the art, that the invention may be combined with measuring methods and devices known per se for simultaneous measuring of parameters other than birefringence. While the measuring object above is described as a compact disc, it should be apparent, however, that the invention may be applied for testing and measuring other optical storage media or data carriers. Furthermore, the polarization modifying means 22 and 24 in the device may be replaced by other means with the purpose of providing perfectly circular polarization at the arrival of the light to the optical data carrier. As reference elements during the calibration process other means may be used than the means 30 and 31 described above, as long as such means fulfil the functional demands according to the description above.

The description above of the invention and the preferred embodiment thereof has an exemplifying but not limiting purpose. Hence, the invention may be exercised in other forms than the ones described above within the scope of the appended patent claims.

We claim:

1. A device for measuring birefringence in an optical data carrier, comprising: a laser light source with polarization modifying means, a beamsplitter, a polarizer, a photodetector, and a controller operatively connected to the photodetector, wherein the laser light source is arranged to illuminate various spots on the optical data carrier with a laser beam through the beamsplitter and the polarizer, wherein the photodetector is arranged to receive a laser beam reflected from the optical data carrier, convert the laser beam into an electric signal and supply it to the controller, and wherein the controller is arranged to determine, from the electric signal received from the photodetector, a birefringence value for the illuminated spot on the optical data carrier, further comprising a transparent reference element with known birefringence properties, a mirror arranged in a vicinity of the optical data carrier and the reference element, and means for directing a laser beam incident from the laser light source towards the reference element in a first calibration position, directly towards the mirror in a second calibration position, and towards the optical data carrier during non-calibration time, wherein the controller is arranged to calculate a first calibration value, corresponding to a given birefringence in the optical data carrier, from the electric signal received from the photodetector in the first calibration position; calculate a second calibration value, corresponding to a situation essentially without any birefringence at all in the optical data carrier, in the second calibration position, and use these calibration values for determining the birefringence in a given spot on the optical data carrier.

2. The device according to claim 1 further comprising a rotating polarizer, by means of which a maximum intensity and a minimum intensity, respectively, is determined for the reflected laser beam.

3. The device according to claim 2, wherein the controller is arranged to determine the birefringence in a given spot on the optical data carrier by means of the values for maximum and minimum light intensity.

4. The device according to claim 1, wherein the light from the laser light source is perfectly circularly polarized when arriving at the optical data carrier, regardless of the polarization of the laser light source.

5. The device according to claim 4, wherein the controller is arranged to use the formula $$BR = \lambda * \left( \frac{1}{4} - \frac{1}{\pi} \arctan\left[ \sqrt{\frac{I_{min}}{I_{max}}} \right] \right)$$

where BR is a value of birefringence, $\lambda$ is the wavelength of the laser light, $I_{min}$ is the minimum light intensity, and $I_{max}$ is the maximum light intensity, when determining the birefringence in a given spot on the optical data carrier.

6. The device according to claim 1, wherein the optical data carrier is rotatable and shaped as a disc.

7. The device according to claim 6, wherein the means comprise a mirror, which is displaceable along the radial direction of the optical data carrier.

8. The device according to claim 6 wherein the optical data carrier is a compact disc.

9. A method of measuring birefringence in an optical data carrier, wherein the data carrier is illuminated by laser light and the light reflected from the data carrier is received and analyzed, so as to determine birefringence values for the data carrier in illuminated spots thereon, comprising the steps of receiving and analyzing laser light reflected from a first reference element in a first mode of calibration, said first reference element having known phase retardation characteristics which essentially correspond to a high level, preferably a maximum level, of birefringence for said data carrier, receiving and analyzing laser light reflected from a second reference element in a second mode of calibration, said second reference element having known phase retardation characteristics which essentially correspond to a low level, preferably a zero or minimum level, of birefringence, and using the measurement results obtained during the first and second mode of calibration, respectively, when calculating and determining an actual birefringence value for the data carrier.

* * * * *